United States Patent
Desarzens et al.

(10) Patent No.: US 7,326,198 B2
(45) Date of Patent: Feb. 5, 2008

(54) REMOTE RELEASE INSTRUMENT HOLDER FOR SURGICAL USE

(75) Inventors: Yves Desarzens, Corgemont (CH); Philippe Fehlbaum, Lignieres (CH); Andre Lechot, Orvin (CH)

(73) Assignee: Precimed S.A., Orvin (CH)

( * ) Notice: Subject to any disclaimer, the term of this patent is extended or adjusted under 35 U.S.C. 154(b) by 472 days.

(21) Appl. No.: 11/006,485

(22) Filed: Dec. 7, 2004

(65) Prior Publication Data

US 2005/0124981 A1  Jun. 9, 2005

Related U.S. Application Data

(63) Continuation-in-part of application No. 10/391,464, filed on Mar. 18, 2003, now Pat. No. 7,056,317, which is a continuation of application No. 09/902,369, filed on Jul. 9, 2001, now Pat. No. 6,540,739, which is a continuation of application No. 09/602,341, filed on Jun. 24, 2000, now Pat. No. 6,264,647.

(60) Provisional application No. 60/527,748, filed on Dec. 9, 2003.

(51) Int. Cl.
    *A61B 17/00* (2006.01)
(52) U.S. Cl. ............................ 606/1; 606/80
(58) Field of Classification Search ............ 606/79–81, 606/180; 279/93, 145
    See application file for complete search history.

(56) References Cited

U.S. PATENT DOCUMENTS

| | | | |
|---|---|---|---|
| 5,236,433 A | 8/1993 | Salyer | |
| 5,658,290 A | 8/1997 | Lechot | |
| 5,817,096 A * | 10/1998 | Salyer | .......................... 606/81 |
| 6,102,915 A * | 8/2000 | Bresler et al. | ................. 606/80 |
| 6,258,107 B1 * | 7/2001 | Balazs et al. | ................ 606/153 |
| 6,264,647 B1 | 7/2001 | Lechot | |
| 6,854,742 B2 * | 2/2005 | Salyer et al. | .................. 279/93 |

\* cited by examiner

*Primary Examiner*—Roy D. Gibson
(74) *Attorney, Agent, or Firm*—Moetteli & Associes SaRL

(57) ABSTRACT

An instrument holder (10) for surgical use has a remote locking mechanism (12) and is elongated having a proximal end (14) and a distal end (16). The holder (10) has an elongated shank (20), a ring (22), a locking component (28) and a spring (32). The elongated shank (20) is equipped, at the distal end (16), with a head (26) adapted to receive an instrument (24). The locking component (28) is substantially cylindrical, elongated and is biased in a first direction (30) toward the head (26) by a spring (32). The locking component (28) includes structures (34) capable of locking the instrument (24) onto the distal end (16). The ring (22) is biased by the spring (32) in a second direction (36) against the locking component (28) towards the proximal end (14) constrained to slide longitudinally on the shank (20), at the proximal end. The remote locking mechanism (12) permits releasable connection to the shank (20) and is engaged by rotation of the ring (22) such that release of the ring from the shank allows the spring (32) and locking component (28) to slide freely off the shank in order to permit cleaning of the instrument holder.

15 Claims, 5 Drawing Sheets

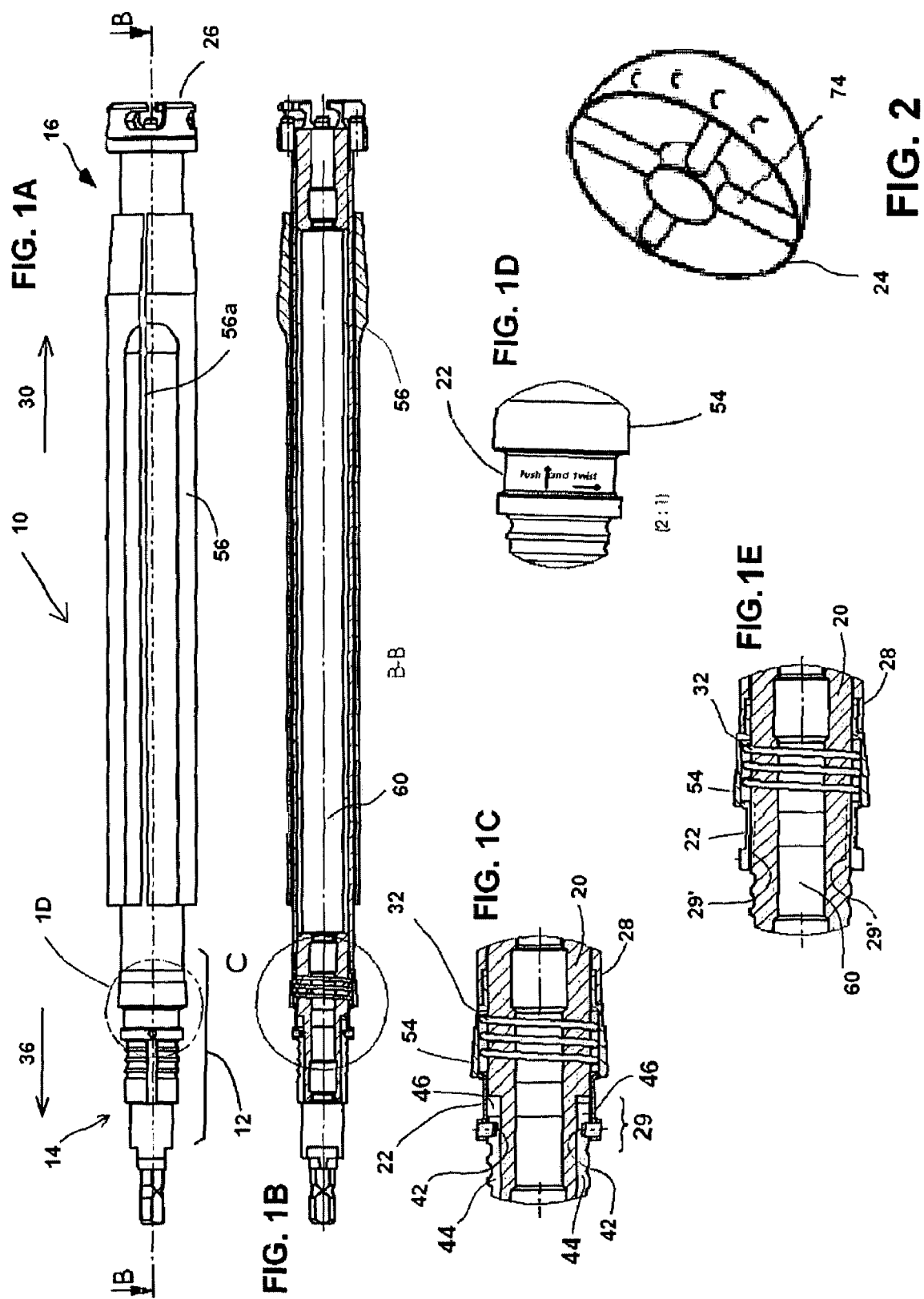

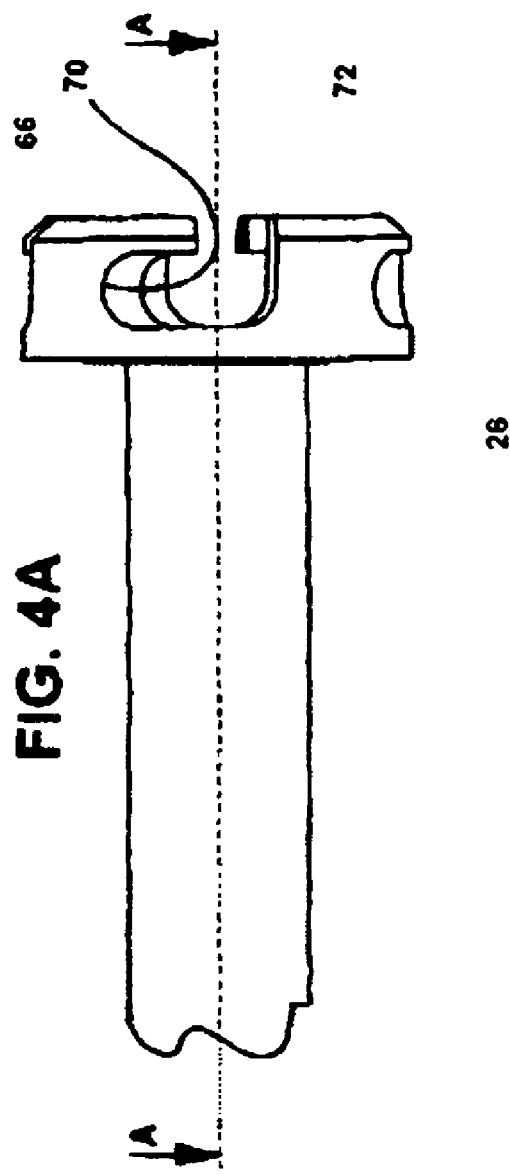
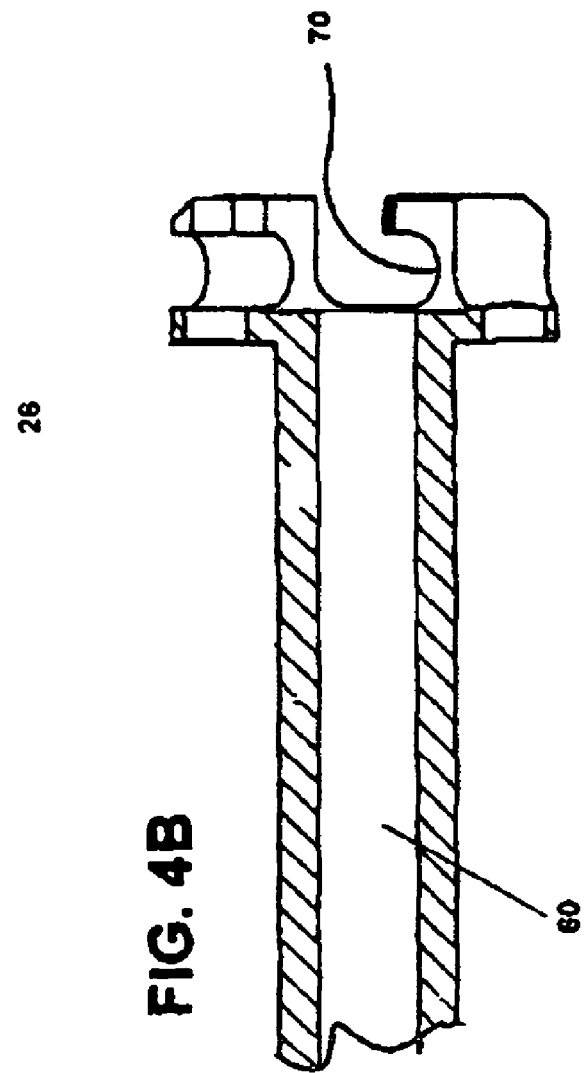
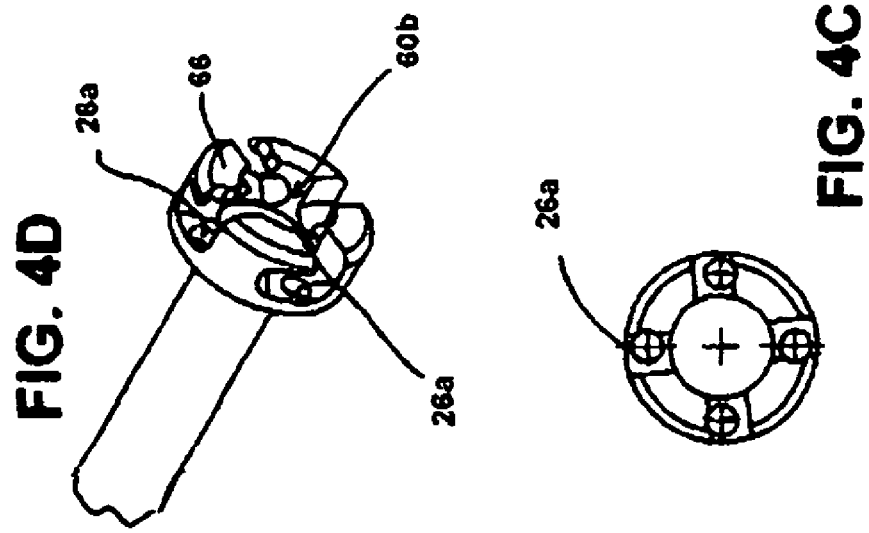
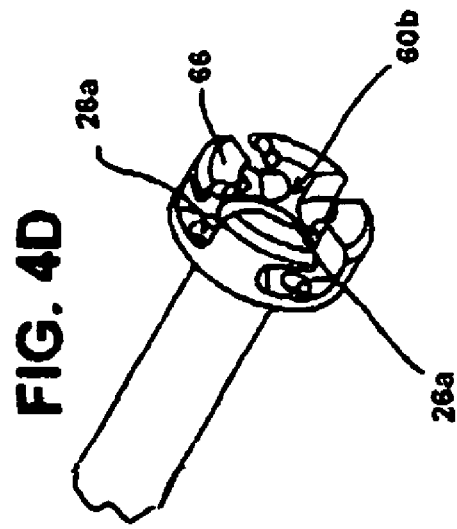

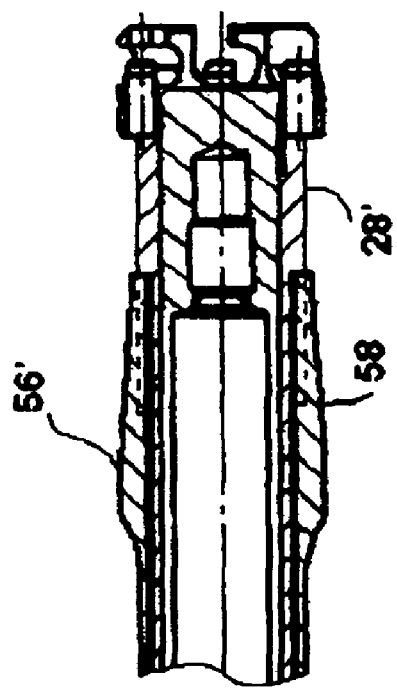
FIG. 6A
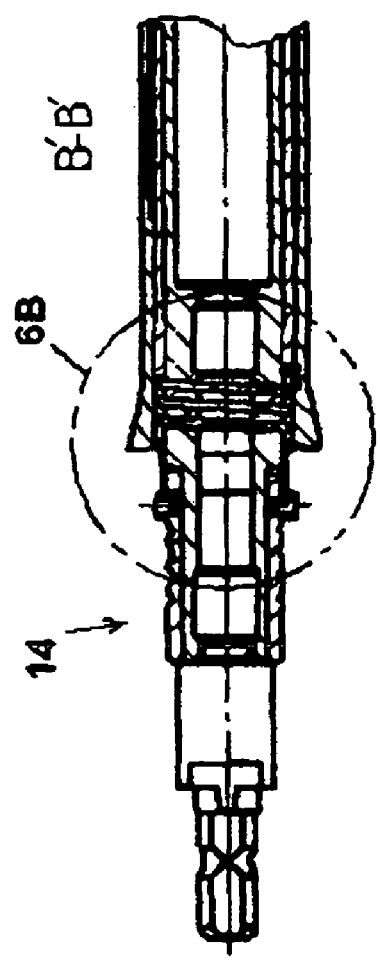
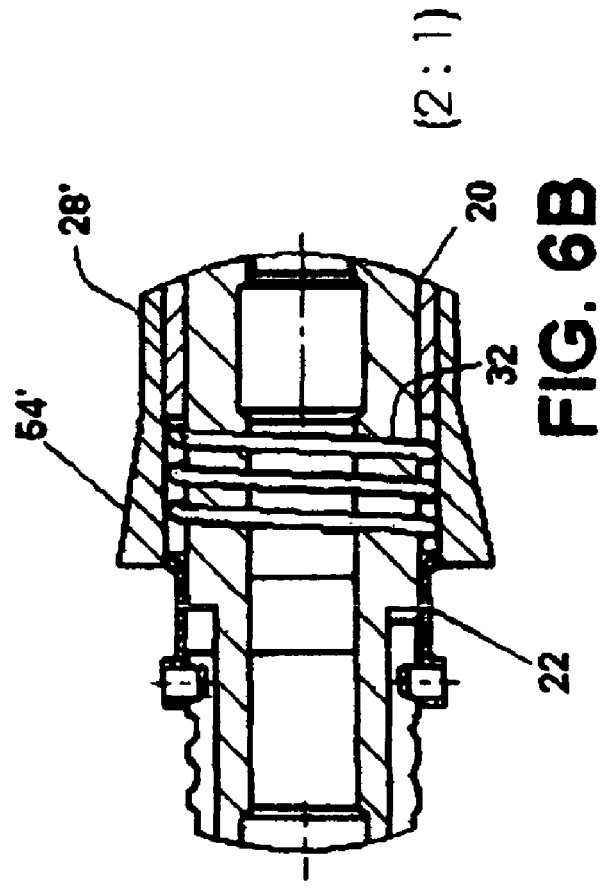
FIG. 6B

REMOTE RELEASE INSTRUMENT HOLDER FOR SURGICAL USE

CROSS REFERENCE TO RELATED APPLICATIONS

This application is a continuation-in-part of a continuation Ser. No. 10/391,464, filed Mar. 18, 2003, now U.S. Pat. No. 7,056,317, which is a continuation of Ser. No. 09/902,369 filed on Jul. 9, 2001, now U.S. Pat. No. 6,540,739 which in turn is a continuation of Ser. No. 09/602,341 filed Jun. 24, 2000 and now U.S. Pat. No. 6,264,647 issued Jul. 24, 2001. Priority is claimed to U.S. provisional application 60/527, 748 filed Dec. 9, 2003. The contents of the above applications and patent are incorporated herein by reference thereto and relied upon.

BACKGROUND OF THE INVENTION

The invention relates to an instrument holder for a surgical instrument, comprising a shank equipped with a head designed to receive an instrument, and an annular locking component mounted so as to slide about the shank, under the head, equipped with locking means which cooperate with the head so as to lock the instrument on the head, and pushed against the head by a helical spring.

An instrument holder of this type is known in particular from U.S. Pat. No. 5,658,290 and U.S. Pat. No. 5,236,433, the contents of which are incorporated herein by reference.

A surgical instrument, for example for preparing for the fitting of a hip prosthesis, works in a medium which causes considerable soiling of the instrument and the instrument holder. Moreover, a surgical instrument holder must be cleaned very frequently and very carefully in order to avoid any risk of infection. However, cleaning of surgical instruments is difficult, in particular cleaning of the space between the shank and the locking component on account of the presence of bone debris and coagulated blood.

Still further, surgical procedures in total hip replacement are becoming more focused on being minimally invasive. The incision is reduced to a minimum possible for the implant size (50 mm in some cases). One such procedure involves the insertion of an acetabular reamer through one incision and the reamer holder through another incision. In larger patients, the current release mechanisms are in the patient's body or too close to it to be operable. With small incisions, the problem is compounded. Further, passing the reamer into the wound can be difficult with the handle attached. Surgeons may wish to remove the reamer in the wound (in the acetabulum) to verify, size, bone condition and eventual implant orientation. Such features require that the surgeon be able to connect and disconnect the tool remotely, from an actuator that is outside the patient's body. In larger patients, the present release mechanisms are in the wound or inaccessible. Again, with small in incisions the problem is compounded.

What is needed therefore is an instrument holder that is simple to disassemble for cleaning without special tools, and which a surgeon can operate remotely, installing or removing a reamer or other tool in situ, while the tool is inside a cavity or incision in the patient.

SUMMARY OF THE INVENTION

An instrument holder for surgical use is provided which has a remote locking mechanism and is elongated having a proximal end and a distal end. The holder has an elongated shank, a ring, and a locking component. The elongated shank is equipped, at the distal end, with a head adapted to receive an instrument. The locking component is substantially cylindrical elongated and is biased in a first direction toward the head by a spring. The locking component includes structures capable of locking the instrument onto the distal end. The ring is biased by the spring in a second direction against the locking component towards the proximal end constrained to slide longitudinally on the shank, at the proximal end. The remote locking mechanism permits releasable connection to the shank and engaged by rotation of the ring such that release of the ring from the shank allows the spring and locking component to slide freely off the shank in order to permit cleaning of the instrument holder.

The object of the invention is to provide an instrument holder that is simple to disassemble for cleaning without special tools, and which a surgeon can actuate remotely, that is remote from the distal end which holds the tool) thus enabling the installation or removal of the reamer or other tool in s, while the tool is inside a cavity or incision in the patient, even a large patient for which the distance from an portion of the holder that a surgeon may grip is considerably displaced from the tool engaging end in the cavity.

To this end, the instrument holder according to the invention has a quick release head which holds the instrument and a locking mechanism which is remote to this quick release head. This improvement over the prior art is realized by simply increasing the length of the locking component in order to move the locking mechanism back away from the attachment head, and then inserting a handle in the form of a sleeve over the elongated portion of the locking component. Further, compared to the prior art, the diameter of the shank is increased and constructed as a tube in order for the diameter to more closely correspond to a diameter required of the handle for ergonomic handling and operation.

The fastening and release of the ring takes place instantaneously, which represents a time savings. This makes it possible to ensure that a complete kit of instruments is not rendered unusable because a single component becomes inoperative.

BRIEF DESCRIPTION OF THE DRAWINGS

The attached drawing shows an embodiment of the invention by way of example.

FIG. 1A is a side view of the instrument holder of the invention.

FIG. 1B is a side, cross-sectional view of the instrument holder of the invention.

FIG. 1C is a detail cross-sectional view of the remote release mechanism of the invention.

FIG. 1D is a detail view of the remote release mechanism of the invention.

FIG. 1E is a detail view of an alternate embodiment of the remote release mechanism of the invention.

FIG. 2 is a perspective view of an instrument for use with the invention.

FIG. 4A is a side view of the head of the invention.

FIG. 4B is a cross sectional side view of the head of the invention

FIG. 4C is a front view of the head of the invention.

FIG. 4D is a perspective view of the head of the invention.

FIG. 6A is a side, cross-sectional view of an alternate embodiment of the invention.

FIG. 6B is a detail view of portion 6B, the remote locking mechanism of the invention, shown in FIG. 6A.

DETAILED DESCRIPTION OF THE PREFERRED EMBODIMENT(S)

Figure 3:
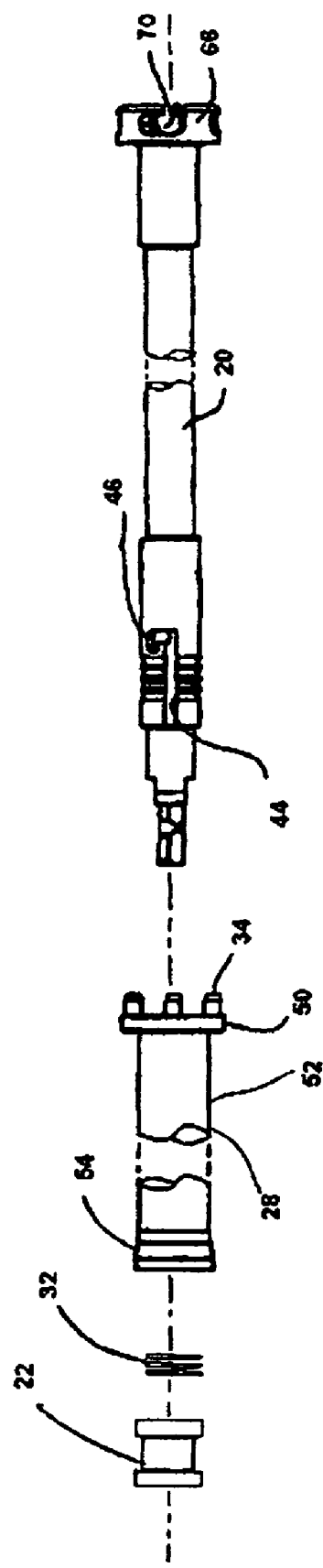
FIG. 3 is an exploded view of a central drive shaft and locking component of the invention.

Referring now to FIGS. 1A-1D, the instrument holder 10 for surgical use has a remote locking mechanism 12, is elongated having a proximal end 14 and a distal end 16 at opposite ends thereof. The holder 10 has an elongated shank 20, a ring 22, and a locking component 28. The elongated shank 20 is equipped, at the distal end, with a head 26 adapted to receive an instrument 24 (shown in FIG. 2) and is configured essentially identically to the head described in U.S. Pat. No. 5,658,290, the content of which is incorporated by reference. The locking component 28 is substantially cylindrical, elongated and is biased in a first direction 30 toward the head 26 by a helical spring 32. The locking component 28 includes structures 34 (shown in FIG. 2) capable of locking the instrument 24 onto the distal end 16. The ring 22 is biased by the spring 32 in a second direction 36 against the locking component 28 towards the proximal end 14 and is constrained to slide longitudinally on the shank 20, at the proximal end. The ring 22 is affixed to the shank 20 by a connection device 29. The remote locking mechanism 12 permits constrained connection to the shank 20 via the connection device 29 which is engaged by rotation of the ring 22. Disengagement of the ring from the shank allows the locking component 28, the spring 32 and the ring 22 to slide freely off the shank in order to permit cleaning of the instrument holder.

Referring now to FIG. 3, the remote locking mechanism 12 preferably includes a bayonet connection device 29 in which the ring 22 is equipped with a bayonet pin 42 placed so as to enter into a bayonet slot 44 and settle into a bayonet recess 46. Two recesses 46 are preferably provided, diametrically opposed on opposite sides of the shank 20, to facilitate assembly.

The locking structures 34 of the locking component 28 are located on the distal end 16 and consist of pins 34 which mount in a face plate 50 which is fixedly attached to a central tubular component 52 of the locking component. On a proximal end 14, the locking component 28 has a raised structure 54 of the form of a frustocone, in order to permit easy gripping by a user, enabling him to push the component back against the force of the spring 32, to remotely release the instrument 24.

Referring again to FIGS. 1A and 1B, an elongated grip 56 is slidingly disposed over the locking component 28 for gripping the holder 10, in a manner that permits sliding of the grip off of the locking component for ease of cleaning and component sterilization. A longitudinal slit 56a is provided in the grip 56 which allows the grip to elastically deform and expand so as to slide over the raised structure 54 when disassembling the holder 10 for cleaning, and is sized so that when compressed such that adjacent surfaces 56b of the slit 56a touch before the inner diameter of the grip bears on the tube. Optionally, the inner surface of the grip 56 includes two diameters, one larger proximal diameter, of a size enabling the grip 56 to slide over the raised structure 54 without disturbing it and the other distal diameter of a size that retains the grip on the locking component 28, being removable therefrom with only a slight elastic deformation. This better enables the operator to control the instrument holder 10 without inadvertently activating the remote locking mechanism 12.

In an alternate embodiment, the shank 20 has an elongated cavity 60 extending through the holder 10 from the distal end 16 to the proximal end 14, to permit evacuation of debris. The holder 10 typically holds a cutter 24 which, when cutting, generates cutting debris (not shown).

Referring now to FIGS. 4A to 4D, the head 26 has a central recess 60b which defines a crown 66 around this recess. This crown 66 has four bayonet catches 70 diametrically opposite in pairs. The instrument 24 is fixed and locked in the catches 70 by the annular locking component 28. The pins 34 are parallel to each other, are aligned parallel to the axis 72 of the shaft 20 and pass through the head 26 in order to close the bayonet catches 70 around elements 74 of the instrument 24, as is described in '290 patent.

Referring now to FIG. 1C, the locking component 28 slides on the shank 20. Also arranged around this shank 20, at the proximal end 14, remote from the head 26, is the spring 32 which engages the raised structure 54 of the locking component 28 and bears against this locking component. Starting from the disassembled position shown in FIG. 2, and in order to assemble the instrument holder 10, the locking component 28 is brought under the head 26, engaging its locking fingers 34 through holes 26a in the head. Then, the spring 32 is slid over the shank 20. Then the rug 22 also slides on the shank 20, and is equipped internally with radial studs 42 that are captured in bayonet slots 44, thus permitting the ring to move axially along the shank 20, and eventually into the bayonet recess 46, when the ring is turned in a manner directed in FIG. 1D. Be means of the ring 22, the spring 32 is pushed against the locking component 28 and compressed while, at the same time, the ring 22 is turned in a counterclockwise direction until its stud 42 engages in the bayonet catch 46 or respectively in one of the bayonet catches, in which the stud is biased by the spring 32. The ring 22 captures the functional components of the assembly together. The assembly of the instrument holder 10 is completed by the grip 56, made of a flexible plastic material and having a longitudinal slit 56a along its side, so as to permit the grip to bias open and slide past the raised structure 54 onto the shank 20. Note that the grip 56 may be placed over the locking component 28 as a first step in the assembly process as well. The instrument holder 10 is then ready for use. The raised structure 54 provides a grip for the thumb and index finger for pulling the locking component 28 back counter to the action of the spring 32 in order to release any instrument 24 that might be fixed on the head 26.

Conversely, in order to disassemble the instrument holder 10, it suffices to first push the ring 22 forward toward the distal end 16 counter to the action of the spring 32. This removes the wedging bias on the pins 42 into the bayonet recesses 46, and permits the surgeon to rotate the ring out of the recesses 46, in line with the bayonet slots 44. Now the surgeon is able to slide the ring 22, spring 32 and the locking component 28 off of the spindle 20.

Unlike the prior art, the actuation mechanism 12 is remote from the head 26 which holds the instrument 24. This is accomplished essentially by increasing the length of the locking component 28 in order to move the locking mechanism 12 back away from the attachment head 26, and then placing the grip 56 over the elongated portion of the locking component 28. The diameter of the shank 20 is increased and constructed as a tube in order for its diameter to more closely correspond to the diameter of the grip 56.

As is shown in FIG. 3, the components 22, 28, and 32 can be completely removed from the shank 20.

Figure 5:
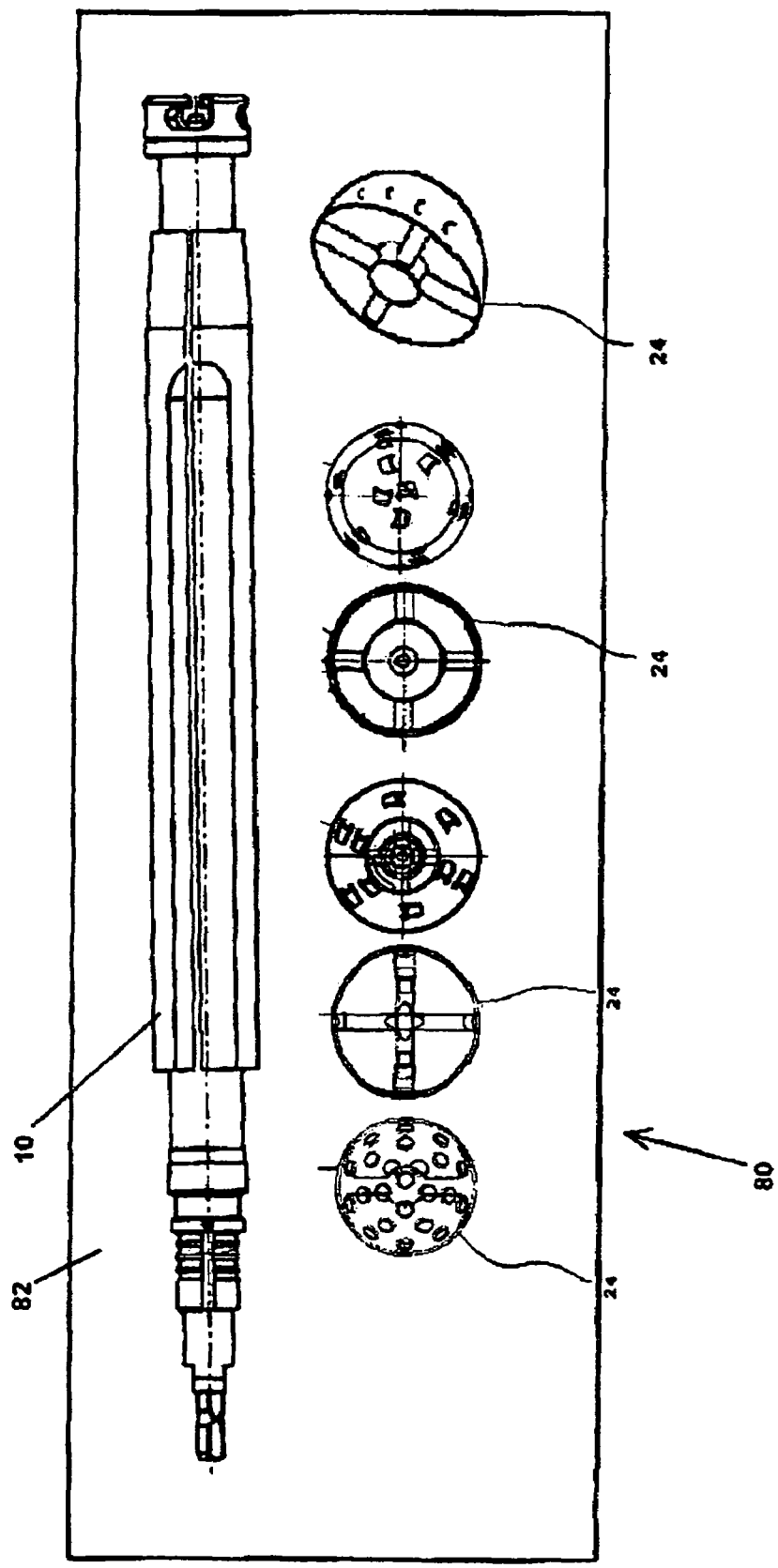
FIG. 5 is a perspective view of a kit of the invention.

Referring now to FIG. 5, a kit 80 of the invention is shown, including the instrument holder 10 and an assortment of instruments 24 conveniently organized in a case 82.

Referring now to FIG. 6A-6B, in an alternate embodiment, the grip 56' is rigidly affixed to the locking component 28' and may include a raised portion 54' at the proximal end 14, which aids a user in gripping the locking component to urge the component back against the force of the spring 32. The grip 56 may be insert-molded onto the locking component 28. The raised portion 54' is preferably frustoconical. Further, in another alternate embodiment not separately shown in the drawings but represented by the threading 58 shown in this figure, the grip 56' may be threaded onto the locking component 28 and locked in place, in any known fashion.

In an advantage, an instrument holder 10 is provided that is simple to disassemble for cleaning and then reassemble without special tools, quickly, which represents a time savings.

In another advantage, an instrument holder 10 is provided that a surgeon can operate remotely, installing or removing a reamer or other tool in situ, while the tool is inside a cavity or incision in the patient.

In another advantage, the ability to quickly disassemble the instrument holder 10 makes it possible to ensure that a complete kit of instruments is not rendered unusable because a single component becomes inoperative.

Although illustrative embodiments of the invention 10 have been shown and described a wide range of modification, change and substitution is contemplated in the foregoing disclosure and in some instances, some features of the present invention may be employed without a corresponding use of the other features. Note that use of the head 26 and the fingers 34 is only one example from all the possible means for connection of an instrument Further, the ring 22 could also be attached to the shank 20 by screwing that is to say, having a screw thread 29' (shown in FIG. 1E) in the ring which matches a thread on the shank Accordingly it is appropriate that the appended claims be construed broadly and in a manner consistent with the scope of the invention.

What is claimed:

1. An instrument holder (10) for surgical use having a remote locking mechanism (12), the instrument holder having a proximal end (14) and a distal end (16), the holder comprising:
   (a) an elongated shank (20) equipped, at the distal end, with a head (26) capable of receiving an instrument (24);
   (b) a spring (32);
   (c) a substantially cylindrical, elongated locking component (28) biased in a first direction (30) toward the head by the spring (32) and including structures (34) capable of locking the instrument onto the distal end; and
   (d) a ring (22) biased by the spring (32) in a second direction (36) against the locking component (28) towards the proximal end (14) and constrained to slide longitudinally on the shank (20), at the proximal end (14), the ring (22) having a connection device (29) which locks the ring to the shank, wherein the ring (22), spring (32), locking component (28) and connection device (29) make up the remote locking mechanism (12) and permit releasable connection to the shank such that release of the ring from the shank allows the spring (32) and locking component (28) to slide freely off the shank in order to permit cleaning of the instrument holder.

2. The instrument holder (10) of claim 1, wherein the remote locking mechanism (12) is a bayonet mechanism (22, 42, 44, 46).

3. The instrument holder (10) of claim 1, wherein the remote locking mechanism (12) is threaded engagement by a thread (29').

4. The instrument holder (10) of claim 1, wherein an elongated grip (56) is loosely disposed over the locking component (28) for gripping the holder, in a manner that permits sliding of the grip (56) off of the locking component (28) for ease of cleaning and component sterilization.

5. The instrument holder (10) of claim 4, wherein the grip (56) includes a raised portion (54) at the proximal end (14), which aids a user in gripping the locking component (28) to urge the component back against the force of the spring (32).

6. The instrument holder (10) of claim 5, wherein the grip (56) has a longitudinal slit (56a) allowing the grip to elastically deform and expand so as to slide over the raised portion (54) when disassembling the holder (10) for cleaning.

7. The instrument holder (10) of claim 4, wherein the grip (56) is rigidly affixed to the locking component (28).

8. The holder (10) of claim 7, wherein the grip (56) is insert-molded onto the locking component (28).

9. The instrument holder (10) of claim 7, wherein the grip (56) includes a raised portion (54) at the proximal end (14), which aids a user in gripping the locking component (28) to urge the component back against the force of the spring (32).

10. The instrument holder (10) of claim 9, wherein the raised portion (54) is frustoconical.

11. The instrument holder (10) of claim 7, wherein the grip (56) is threaded onto the locking component (28).

12. The instrument holder (10) of claim 11, wherein the grip (56) includes a raised portion (54) at the proximal end (14), which aids a user in gripping the locking component (28) to urge the component back against the force of the spring (32).

13. The instrument holder (10) of claim 12, wherein the raised portion (54) is frustoconical.

14. The instrument holder (10) of claim 1, wherein the shank (20) has an elongated cavity (60) extending through the holder from the distal end (16) to the proximal end (14), to permit evacuation of debris through the holder from the distal end which is typically a cutting end where cutting generates debris.

15. A kit (80) for surgical use, the kit comprising:
   (a) An instrument holder (10) for surgical use having a remote locking mechanism (12), the instrument holder having a proximal end (14) and a distal end (16), the holder comprising:
      i. an elongated shank (20) equipped, at the distal end, with a head (26) capable of receiving an instrument (24);
      ii. a spring (32);
      iii. a substantially cylindrical, elongated locking component (28) biased in a first direction (30) toward the head by the spring (32) and including structures (34) capable of locking the instrument onto the distal end; and
      iv. a ring (22) biased by the spring (32) in a second direction (36) against the locking component (28) towards the proximal end (14) and constrained to slide longitudinally on the shank (20), at the proximal end (14), the ring (22) having a connection device (29) which locks the ring to the shank, wherein the ring (22), spring (32), locking component (28) and connection device (29) make up the remote locking mechanism (12) and permit releasable connection to the shank such that release of the ring from the shank allows the spring (32) and locking component (28) to slide freely off the shank in order to permit cleaning of the instrument holder;

(b) at least one instrument (24); and (c) a case (82).

* * * * *

UNITED STATES PATENT AND TRADEMARK OFFICE
CERTIFICATE OF CORRECTION

PATENT NO. : 7,326,198 B2 Page 1 of 1
APPLICATION NO. : 11/006485
DATED : February 5, 2008
INVENTOR(S) : Yves Desarzens et al.

It is certified that error appears in the above-identified patent and that said Letters Patent is hereby corrected as shown below:

In Col. 2, line 4, replace the phrase "cylindrical elongated" with --cylindrical, elongated--.

In Col. 2, line 18, replace the phrase "which holds the tool) thus" with --which holds the tool, thus--.

In Col. 2, line 20, replace the phrase "tool in s, while" with --tool in situ while--.

In Col. 2, line 21, replace the phrase "the distance from an" with --the distance from a--.

In Col. 4, line 25, replace the phrase "rug 22 also slides" with --ring 22 also slides--.

In Col. 4, line 29, replace the phrase "Be means of the ring" with --By means of the ring--.

Signed and Sealed this

Twenty-second Day of July, 2008

JON W. DUDAS
*Director of the United States Patent and Trademark Office*

UNITED STATES PATENT AND TRADEMARK OFFICE
CERTIFICATE OF CORRECTION

PATENT NO. : 7,326,198 B2  
APPLICATION NO. : 11/006485  
DATED : February 5, 2008  
INVENTOR(S) : Desarzens et al.

Page 1 of 1

It is certified that error appears in the above-identified patent and that said Letters Patent is hereby corrected as shown below:

Column 1 delete the paragraph spanning lines 7-16:

"This application is a continuation-in-part of a continuation Ser. No. 10/391,464, filed Mar. 18, 2003, now U.S. Pat. No. 7,056,317, which is a continuation of Ser. No. 09/902,369 filed on Jul. 9, 2001, now U.S. Pat. No. 6,540,739 which in turn is a continuation of Ser. No. 09/602,341 filed Jun. 24, 2000 and now U.S. Pat. No. 6,264,647 issued Jul. 24, 2001. Priority is claimed to U.S. provisional application 60/527,748 filed Dec. 9, 2003. The contents of the above applications and patent are incorporated herein by reference thereto and relied upon."

Column 1 line 7 insert the following paragraph:

--This application is a continuation-in-part of Ser. No. 10/391,464, filed Mar. 18, 2003, now U.S. Pat. No. 7,056,317, which is a continuation of Ser. No. 09/902,369 filed on Jul. 9, 2001, now U.S. Pat. No. 6,540,739 which in turn is a continuation of Ser. No. 09/602,341 filed Jun. 24, 2000 and now U.S. Pat. No. 6,264,647 issued Jul. 24, 2001. Priority is claimed to U.S. provisional application 60/527,748 filed Dec. 9, 2003. The contents of the above applications and patent are incorporated herein by reference thereto and relied upon.--

Signed and Sealed this  
Twenty-eighth Day of August, 2012

David J. Kappos  
*Director of the United States Patent and Trademark Office*